United States Patent
Parker

(10) Patent No.: US 8,509,461 B2
(45) Date of Patent: *Aug. 13, 2013

(54) BONE CONDUCTION DEVICES GENERATING TANGENTIALLY-DIRECTED MECHANICAL FORCE USING A ROTATIONALLY MOVING MASS

(75) Inventor: John L. Parker, Roseville (AU)

(73) Assignee: Cochlear Limited, Macquarie University, NSW (AU)

( * ) Notice: Subject to any disclaimer, the term of this patent is extended or adjusted under 35 U.S.C. 154(b) by 488 days.

This patent is subject to a terminal disclaimer.

(21) Appl. No.: 12/688,491

(22) Filed: Jan. 15, 2010

(65) Prior Publication Data

US 2010/0121134 A1 May 13, 2010

Related U.S. Application Data

(63) Continuation of application No. 12/398,586, filed on Mar. 5, 2009, and a continuation of application No. 12/398,539, filed on Mar. 5, 2009, now abandoned.

(60) Provisional application No. 61/041,185, filed on Mar. 31, 2008.

(51) Int. Cl.
*H04R 25/00* (2006.01)

(52) U.S. Cl.
USPC ........... 381/150; 381/151; 381/173; 381/312; 381/328; 600/25; 607/57

(58) Field of Classification Search
USPC ........... 381/150, 151, 173, 312, 328; 600/25; 607/57
See application file for complete search history.

(56) References Cited

U.S. PATENT DOCUMENTS

| | | | |
|---|---|---|---|
| 4,352,960 A | 10/1982 | Dormer et al. | |
| 4,612,915 A | 9/1986 | Hough et al. | |
| 5,735,790 A | 4/1998 | Håkansson et al. | |
| 5,935,170 A | 8/1999 | Håkansson et al. | |
| 6,751,334 B2 | 6/2004 | Hakansson | |
| 2001/0031908 A1 | 10/2001 | Buschek et al. | |
| 2004/0210103 A1 | 10/2004 | Westerkull | |
| 2006/0082158 A1 | 4/2006 | Schrader | |
| 2008/0255406 A1* | 10/2008 | Ball et al. | 600/25 |
| 2009/0252353 A1* | 10/2009 | Parker | 381/151 |

FOREIGN PATENT DOCUMENTS

| | | | |
|---|---|---|---|
| WO | 0193634 A1 | 12/2001 | |
| WO | 03001845 A1 | 1/2003 | |

OTHER PUBLICATIONS

Vermiglio et al. "A Measurement of Sound Level Perception when using the Bone-Anchored Hearing Aid (BAHA) for Trans-Cranial Stimulation of Individuals with Single-Sided Deafness" House Ear Institute. Advanced Hearing Science, International Hearing Aid Research Conference. Aug. 2004.

* cited by examiner

*Primary Examiner* — Daniel Whalen
*Assistant Examiner* — Suberr Chi
(74) *Attorney, Agent, or Firm* — Kilpatrick, Townsend & Stockton, LLP

(57) ABSTRACT

A bone conduction device, comprising: a sound input element configured to receive an acoustic sound signal; an electronics module configured generate an electrical signal representing said acoustic sound signal; and a transducer, comprising a mass configured to move in a rotational direction, configured to generate a vibrational force in a tangential direction with respect to a recipient's bone.

24 Claims, 7 Drawing Sheets

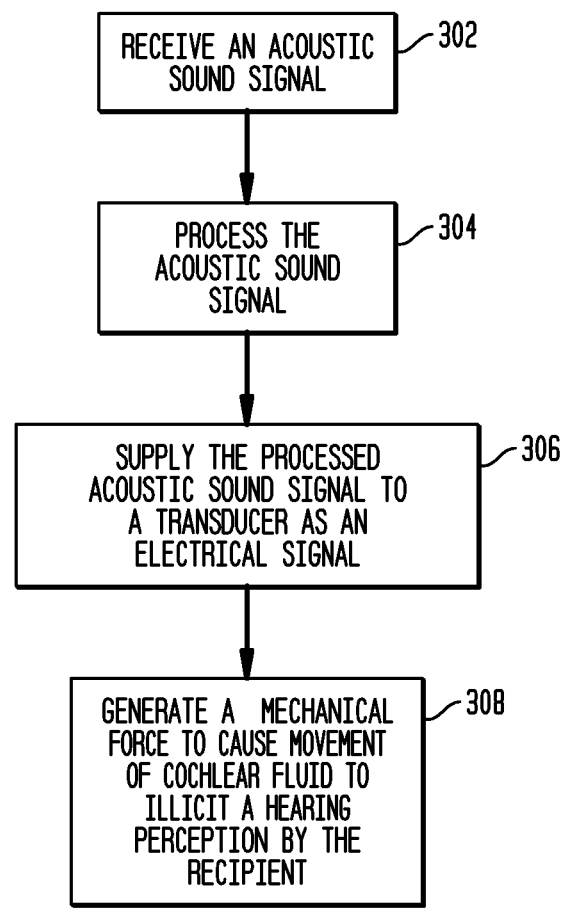

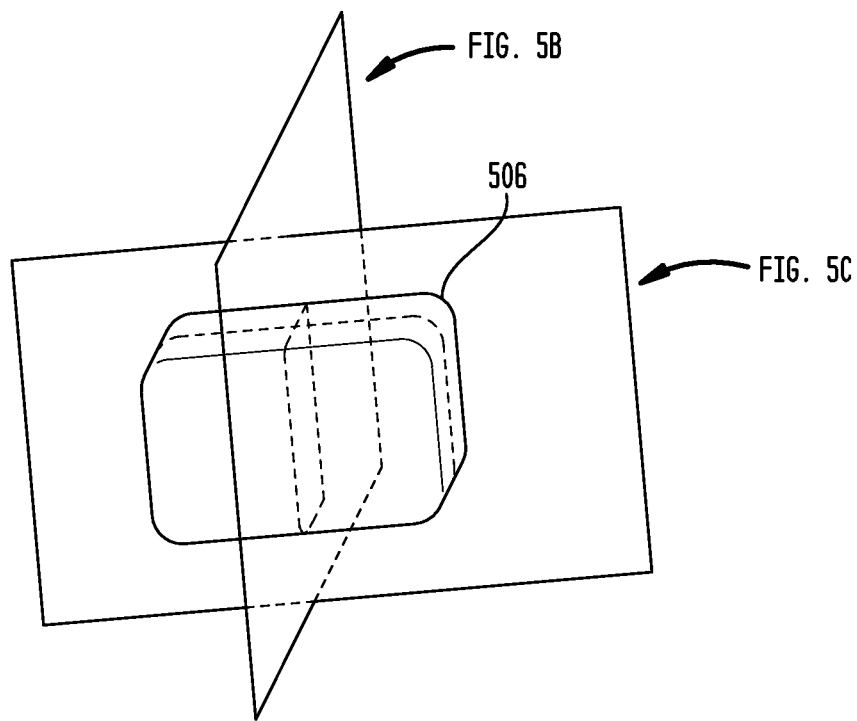
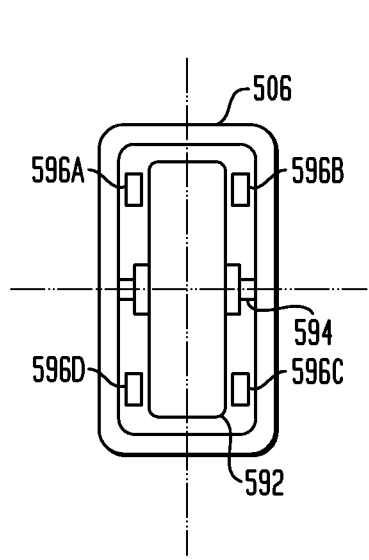
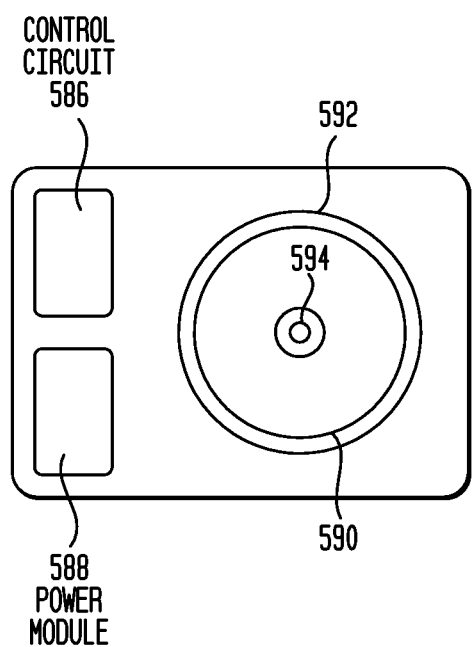

BONE CONDUCTION DEVICES GENERATING TANGENTIALLY-DIRECTED MECHANICAL FORCE USING A ROTATIONALLY MOVING MASS

CROSS-REFERENCE TO RELATED APPLICATIONS

The present application is a continuation of U.S. patent application Ser. No. 12/398,586, filed Mar. 5, 2009. The present application is also a continuation of U.S. patent application Ser. No. 12/398,539, filed on Mar. 5, 2009 which claims the benefit from U.S. Provisional Patent Application 61/041,185; filed Mar. 31, 2008. The contents of these applications are hereby incorporated by reference herein.

BACKGROUND

1. Field of the Invention

The present invention relates generally to prosthetic hearing devices, and more particularly, to a bone conduction hearing devices generating stimulation via tangentially-directed vibrational force with respect to a surface of the recipient's bone.

2. Related Art

There are three basic types of hearing loss: sensorineural, conductive, and mixed hearing losses. Sensorineural hearing loss results from damage to the inner ear or to the nerve pathways from the inner ear to the brain. The majority of human sensorineural hearing loss is caused by abnormalities or damage to the hair cells in the cochlea. Hair cells in the cochlea are the sensory receptors that transduce sound to nerve impulses. Acoustic hearing aids may be appropriate for those who suffer from mild to moderate sensorineural hearing loss. In cases of severe or profound sensorineural hearing loss, a cochlear implant may be the appropriate choice. Cochlear implants bypass the hair cells in the cochlea and directly stimulate the auditory nerve fibers in the cochlea by an electrode array that is implanted in the cochlea. Simulation of the auditory nerve fibers creates the sensation of hearing in the recipient.

Conductive hearing loss occurs when there is a problem with the conduction of sound from the external or middle ear to the inner ear. This type of hearing loss may be caused by anything that impedes the motion of the ossicles, the three bones of the middle ear that conduct sound to the cochlea. It may also be caused by a failure of the eardrum to vibrate in response to sound or fluid in the middle ear. Conductive hearing loss may be treated by acoustic hearing aids, middle ear implants, and the like.

Still other individuals suffer from mixed hearing losses, that is, conductive hearing loss in conjunction with sensorineural hearing. In other words, there may be damage in both the outer or middle ear and the inner ear (cochlea) or auditory nerve.

While many individuals suffering from conductive hearing loss often use acoustic hearing aids, such hearing aids may not be suitable for all individuals, such as those suffering from chronic ear infections or from single-sided deafness. An alternative treatment is the use of bone conduction hearing aids, or simply conduction devices herein.

Bone conduction hearing aids utilize the bones of an individual's bone to transmit acoustic signals to the cochlea. Generally, most bone conduction hearing aids function by converting a received sound signal into vibration. This vibration is then transferred to the bone structure of the bone, in one particular embodiment the skull. This skull vibration results in motion of the fluid of the cochlea, thereby stimulating the cochlear hair cells and causing the perception of sound in the recipient.

Bone conduction devices may be attached to a titanium implant implanted in a recipient's bone, via an external abutment. In one particular embodiment of the present invention, the titanium implant is surgically implanted into the part of the skull bone that is behind the ear and allowed to naturally integrate with the skull bone over time. The bone conduction device is coupled to the titanium implant via the external abutment. Vibrations from the bone conduction device are then transmitted to the skull through the external abutment and the titanium implant to stimulate nerve fibers of the inner ear of the recipient.

Some bone conduction devices produce sound perception by applying a vibrational force directly to the recipient's bone, which is communicated through the bone eventually to the cochlea where the fluids contained therein are vibrated. In some devices, the vibrational force is directed towards the recipient's bone perpendicularly with respect to the surface of the recipient's bone. In such devices, the angle between the surface of the recipient's bone and the direction of the vibrational force is as close to 90 degrees as possible in order to ensure the most efficient transfer of vibrational force to the recipient's bone as possible. As noted earlier, the transferred vibrational force is conducted through the bone to the recipient's cochlea, causing motion of the cochlear fluid, thereby producing sound perception. It may be possible to cause that movement of cochlear fluid to produce the sound perception in other ways without directly applying and communicating a vibrating vibrational force to the recipient's bone.

SUMMARY

In one aspect of the present invention, a bone conduction device is provided. The bone conduction device comprises: a sound input element configured to receive an acoustic sound signal; an electronics module configured generate an electrical signal representing said acoustic sound signal; and a transducer, comprising a mass configured to move in a rotational direction, configured to generate a vibrational force in a tangential direction with respect to a recipient's bone.

In yet another aspect of the present invention, a method rehabilitating the hearing of a recipient with a bone conduction device is provided. The method comprises rehabilitating the hearing of a recipient with a bone conduction device having an anchor, comprising: forming a mechanical coupling between the bone conduction device and the recipient's bone via the anchor; receiving an electrical signal representative of an acoustic sound signal; generating a vibrational force, using a rotating mass, representative of the received electrical signal, wherein the vibrational force is directed in a tangential direction with respect to the recipient's bone; and delivering said vibrational forces to the recipient's bone via the formed coupling.

BRIEF DESCRIPTION OF THE DRAWINGS

Illustrative embodiments of the present invention are described herein with reference to the accompanying drawings, in which:

FIG. 3 is a flowchart illustrating the conversion of an input sound into movement of cochlear fluid in accordance with embodiments of the present invention;

FIG. 5A is a perspective view of a transducer module of a bone rotating bone conduction device in accordance with embodiments of the present invention;

FIG. 5B is a first cross-sectional view of the transducer module of the bone conduction device illustrated in FIG. 5A in accordance with embodiments of the present invention;

FIG. 5C is a second cross-sectional view of the transducer module of the bone conduction device illustrated in FIG. 5A in accordance with embodiments of the present invention.

DETAILED DESCRIPTION

Embodiments of the present invention are generally directed to a bone conduction device for converting a received acoustic sound signal into a vibrational force that is generated in a tangential direction with respect to the surface of the recipient's bone, which ultimately produces sound perception by the recipient. The tangentially directed vibrational force generated by embodiments of the present invention causes rotation of the skull about the neck and is conducted to the cochlea of the recipient. The conducted force acts on the cochlea to cause motion of the cochlear fluid contained therein, causing the hair cells in the cochlea to be activated to produce sound perception by the recipient.

The bone conduction device receives the acoustic sound signal and generates an electrical signal representing the acoustic sound signal. The bone conduction device includes a transducer which converts the electrical signal into motion of a mass component so as to generate the vibrational force directed in a tangential direction with respect to the surface of the recipient's bone, causing rotation of the recipient's skull about the neck. In certain embodiments of the present invention, the transducer has a flywheel component which rotates about a fixed axis. In those embodiments, one or more coils positioned around the circumference of, and separate from, the flywheel component may be energized so as to pull or push the spinning flywheel from its rotation axis, thereby generating a vibrational force that is directed in a tangential direction with respect to the recipient's skull, to cause it to rotate about the recipient's neck.

In some embodiments, the transducer module may be outside the recipient's skin, attached to a percutaneous anchor system. In other embodiments, the system may comprise the transducer module embedded or implanted under the recipient's skin and further comprise communication components configured to communicate with the implanted transducer module to provide instructions and possibly even power to the implanted transducer.

In various embodiments of the present invention, the transducer may comprise a piezoelectric element that deforms in response to application of the electrical signal thereto, thereby generating vibrational forces. The amount of deformation of a piezoelectric element in response to an applied electrical signal depends on material properties of the element, orientation of the electric field with respect to the polarization direction of the element, geometry of the element, etc.

Figure 1:
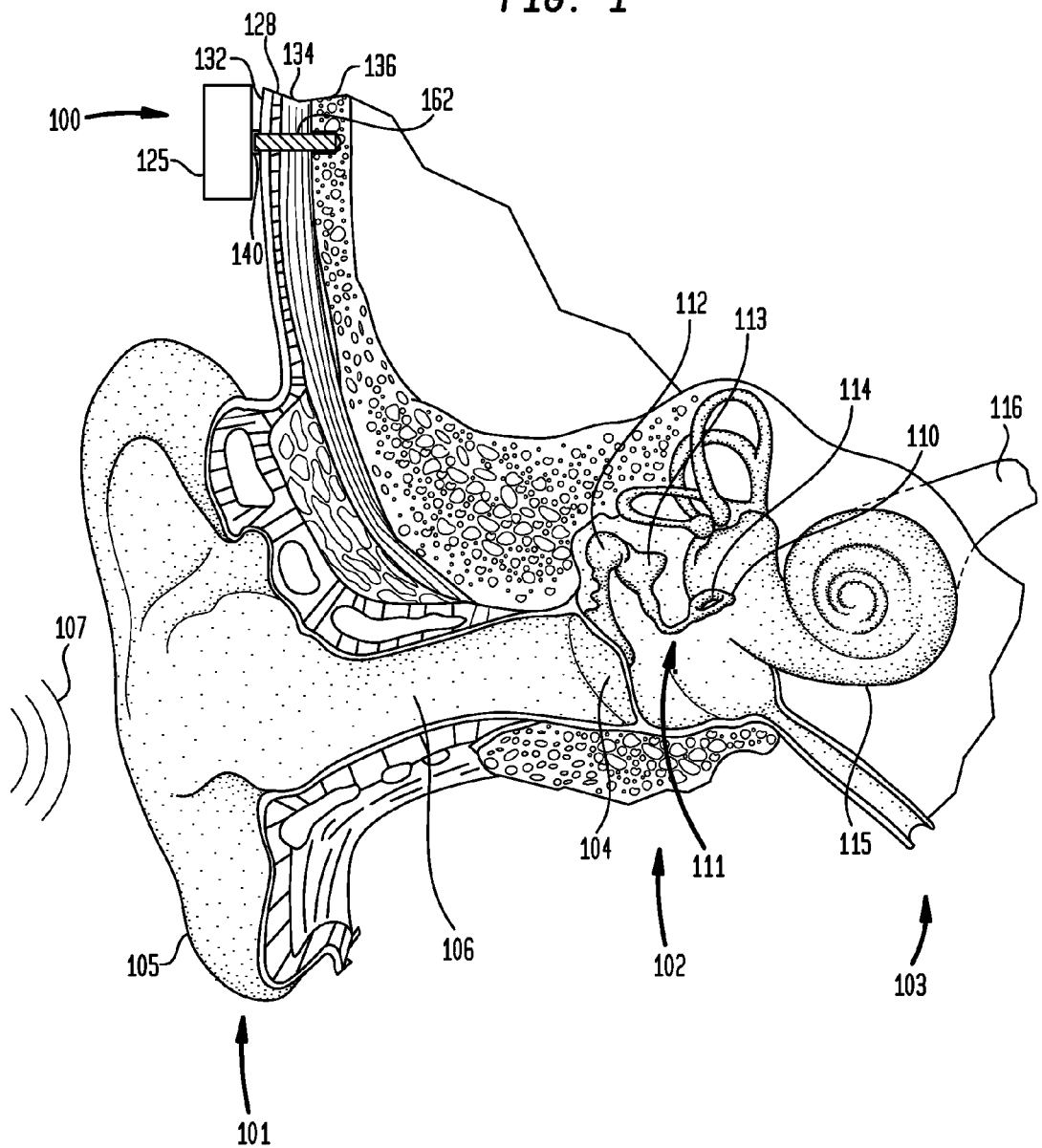
FIG. 1 is a perspective view of a bone-rotating bone conduction device implanted behind a recipient's ear.

FIG. 1 is a perspective view of embodiments of a bone conduction device 100 in which embodiments of the present invention may be advantageously implemented. In a fully functional human hearing anatomy, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 110 through three bones of middle ear 102, collectively referred to as the ossicles 111 and comprising the malleus 112, the incus 113 and the stapes 114. Bones 112, 113 and 114 of middle ear 102 serve to filter and amplify acoustic wave 107, causing oval window 110 to articulate, or vibrate. Such vibration sets up waves of fluid motion within cochlea 115. Such fluid motion, in turn, activates tiny hair cells (not shown) that line the inside of cochlea 115. Activation of the hair cells causes appropriate nerve impulses to be transferred through the spiral ganglion cells and auditory nerve 116 to the brain (not shown), where they are perceived as sound.

FIG. 1 also illustrates the positioning of one embodiment of the present invention bone conduction device 100 relative to outer ear 101, middle ear 102 and inner ear 103 of a recipient of device 100. As shown, bone conduction device 100 may be positioned behind outer ear 101 of the recipient. In the embodiment illustrated in FIG. 1, bone conduction device 100 is an externally fitted embodiment of the present invention and comprises a housing 125 having a microphone (not shown) positioned therein or thereon. Housing 125 is coupled to the body of the recipient via coupling 140 and an anchor system 162. As described below, bone conduction device 100 may comprise a sound processor, a transducer, transducer drive components and/or various other electronic circuits/devices. In accordance with embodiments of the present invention, anchor system 162 may be implanted in the recipient. As described below, anchor system 162 may be fixed to bone 136 and may extend from bone 136 through muscle 134, fat 128 and skin 132 so that coupling 140 may be coupled to the anchor system.

Figure 2A:
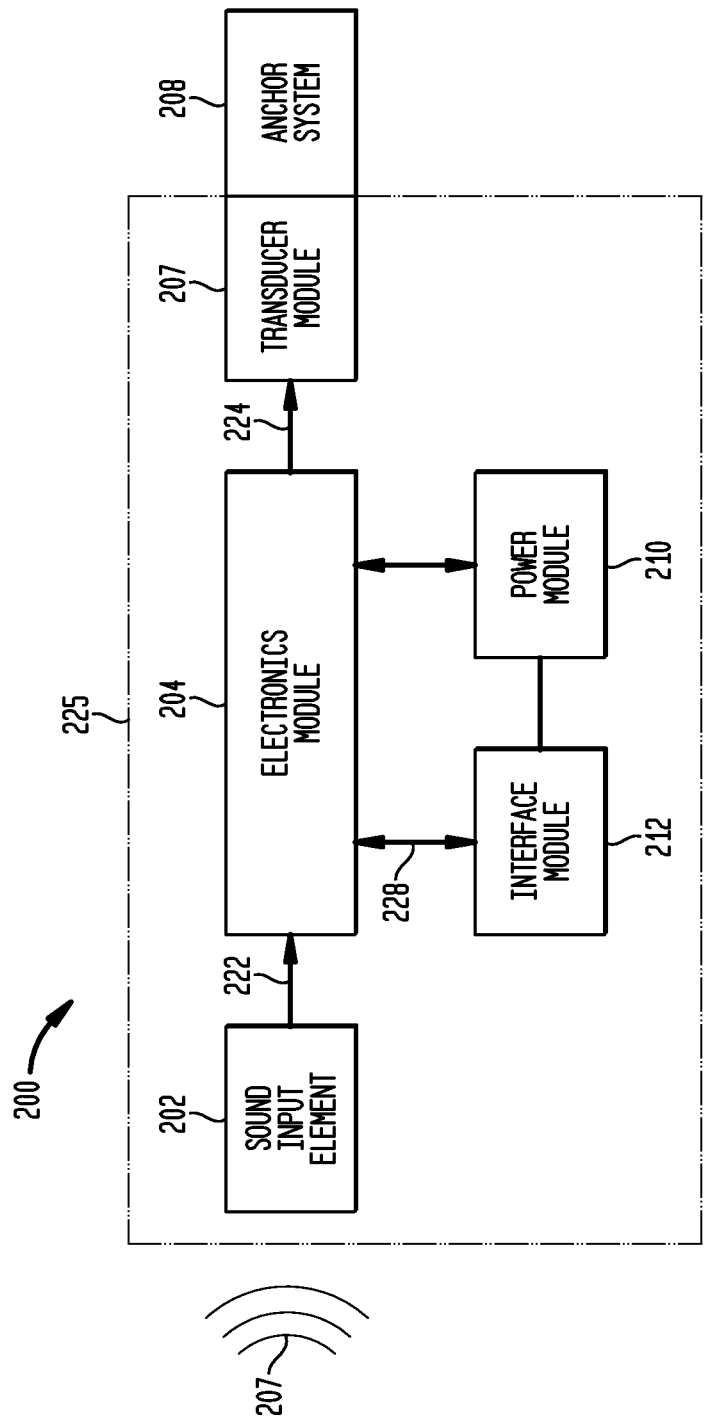
FIG. 2A is a high-level functional block diagram of a bone-rotating bone conduction device, such as the device of FIG. 1.

A functional block diagram of one embodiment of bone conduction 100, referred to as bone conduction device 200, is shown in FIG. 2A. In the illustrated embodiment, a sound wave 207 is received by a sound input element 202. In some embodiments, sound input element 202 is a microphone configured to receive sound wave 207, and to convert sound wave 207 into an electrical signal 222. As described below, in other embodiments, sound wave 207 may be received by sound input element 202 as an electrical signal.

As shown in FIG. 2A, electrical signal 222 is output by sound input element 202 to an electronics module 204. Electronics module 204 is configured to convert electrical signal 222 into an adjusted electrical signal 224. As described below in more detail, electronics module 204 may include a sound processor, control electronics, transducer drive components, and a variety of other elements.

As illustrated in FIG. 2A, transducer module 206 receives adjusted electrical signal 224 and generates a vibrational output force that is directed in a tangential direction with respect to the recipient's bone. The tangentially directed vibrational force is delivered to the skull of the recipient via coupling 140, shown in FIG. 2A as a part of anchor system 208, that is coupled to bone conduction device 200. Delivery of this output force causes the recipient's skull to rotate about the recipient's neck and causes movement or waves of the cochlear fluid, resulting in activating the hair cells in the cochlea to produce sound perception.

FIG. 2A also illustrates a power module 210. Power module 210 provides electrical power to one or more components of bone conduction device 200. For ease of illustration, power module 210 has been shown connected only to interface module 212 and electronics module 204. However, it should be appreciated that power module 210 may be used to supply power to any electrically powered circuits/components of bone conduction device 200.

Bone conduction device 200 further includes an interface module 212 that allows the recipient to interact with device 200. For example, interface module 212 may allow the recipient to adjust the volume, alter the speech processing strategies, power on/off the device, etc. Interface module 212 communicates with electronics module 204 via signal line 228.

In the embodiment illustrated in FIG. 2A, sound pickup device 202, electronics module 204, transducer module 206, power module 210 and interface module 212 have all been shown as integrated in a single housing, referred to as housing 225. However, it should be appreciated that in certain embodiments of the present invention, one or more of the illustrated components may be housed in separate or different housings, one or more of which may be surgically implanted under the recipient's skin. Furthermore, the implanted components may be embedded at least partially within the recipient's bone or otherwise fixed to the bone so as to prevent movement with respect to the bone. Similarly, it should also be appreciated that in such embodiments, direct connections between the various modules and devices are not necessary and that the components may communicate, for example, via wireless connections. Also, where transducer module 206 is outside the recipient's skin, the movement may be communicated via anchor system 208 to the recipient's skull so as to cause the skull to rotate about the recipient's neck. Where transducer module 206 is among the components implanted beneath the recipient's skin, transducer module 206 may be fixed to the recipient's skull through a variety of means so as to communicate the vibrational force to the recipient's skull to cause the skull to rotate about the recipient's neck.

In embodiments of the present invention, transducer module 206 may be one of many types and configurations of transducers, now known or later developed. In one embodiment of the present invention, transducer module 206 may comprise a piezoelectric element which is configured to deform in response to the application of electrical signal 224. Piezoelectric elements that may be used in embodiments of the present invention may comprise, for example, piezoelectric crystals, piezoelectric ceramics, or some other material exhibiting a deformation in response to an applied electrical signal. Exemplary piezoelectric crystals include quartz ($SiO_2$), Berlinite ($AlPO_4$), Gallium orthophosphate ($GaPO_4$) and Tourmaline. Exemplary piezoelectric ceramics include barium titanate ($BaTiO_3O$), lead zirconate titanate (PZT), or zirconium (Zr).

Some piezoelectric materials, such as barium titanate and PZT, are polarized materials. When an electric field is applied across these materials, the polarized molecules align themselves with the electric field, resulting in induced dipoles within the molecular or crystal structure of the material. This alignment of molecules causes the deformation of the material.

In other embodiments of the present invention, other types of transducers may be used. For example, various motors configured to operate in response to electrical signal 224 may be used.

Figure 2B:
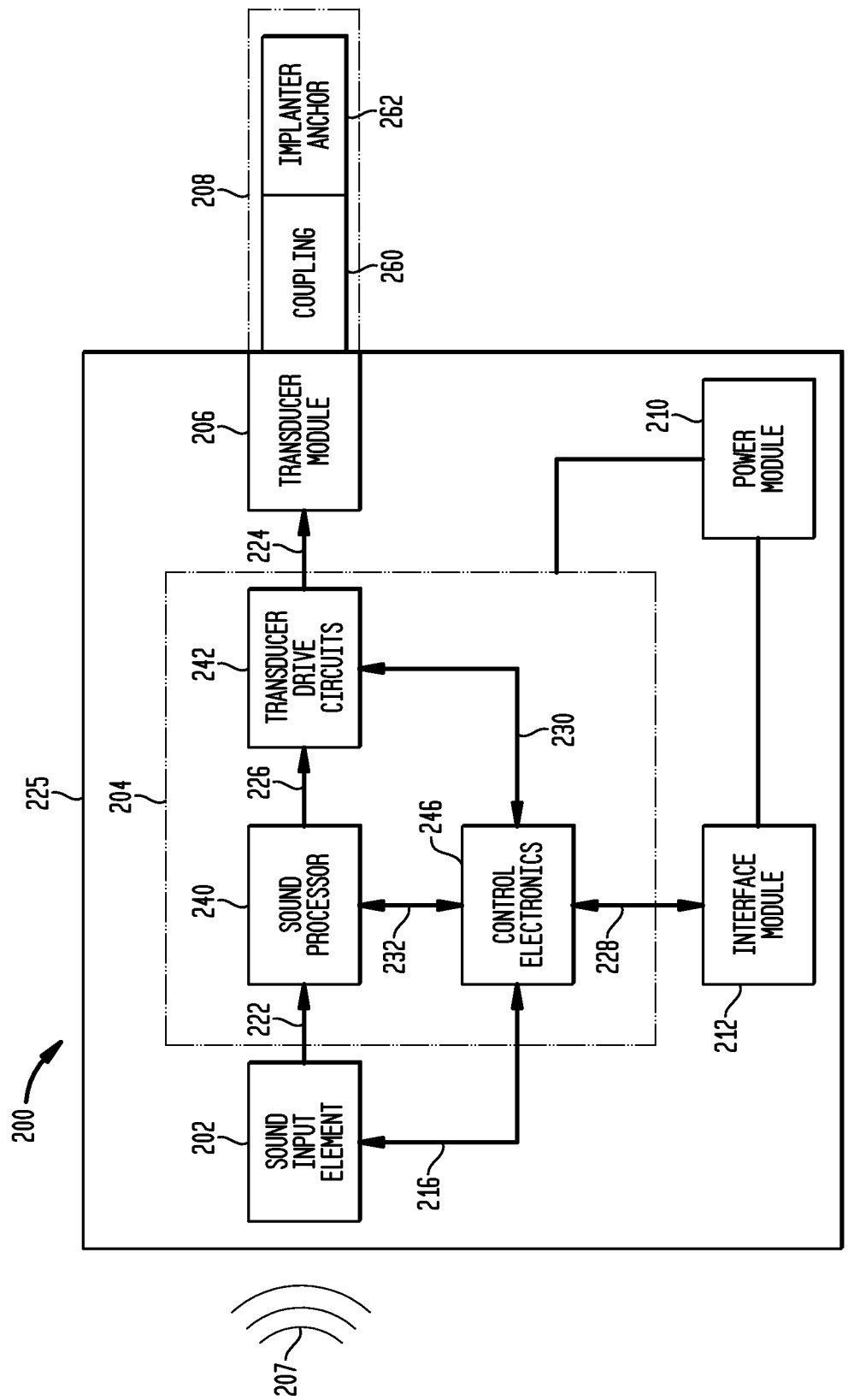
FIG. 2B is detailed functional block diagram of the bone-rotating bone conduction device illustrated in FIG. 2A.

In one embodiment of the present invention, transducer module 206 generates an output force that is directed tangentially with respect to the surface of the recipient's bone. This tangentially directed vibrational force causes rotation of the recipient's skull about the neck, to produce movement of the cochlea fluid so that a sound may be perceived by the recipient. As noted above, in certain embodiments, bone conduction device 200 delivers the output force to the skull of the recipient via an anchor system 208. In one embodiment of the present invention, anchor system 208 comprises a coupling 260 mechanically couples to an implanted anchor 262, as illustrated in FIG. 2B. Vibration from transducer module 206 is provided to anchor system 208 through housing 225.

In certain embodiments of the present invention, electronics module 204 includes a printed circuit board (PCB) to electrically connect and mechanically support the components of electronics module 204. Sound input element 202 may comprise one or more microphones (not shown) and is attached to the PCB.

FIG. 2B provides a more detailed view of bone conduction device 200 of FIG. 2A. In the embodiment illustrated, electronics module 204 comprises a sound processor 240, transducer drive components 242 and control electronics 246. As explained above, in certain embodiments sound input element 202 comprises a microphone configured to convert a received acoustic signal into electrical signal 222. In other embodiments, as detailed below, sound input element 202 receives sound wave 207 as an electrical signal.

In embodiments of the present invention, electrical signal 222 is output from sound input element 202 to sound processor 240. Sound processor 240 uses one or more of a plurality of techniques to selectively process, amplify and/or filter electrical signal 222 to generate a processed signal 226. In certain embodiments, sound processor 240 may comprise substantially the same sound processor as is used in an air conduction hearing aid. In further embodiments, sound processor 240 comprises a digital signal processor.

Processed signal 226 is provided to transducer drive components 242. Transducer drive components 242 output a drive signal 224, to transducer module 206. Based on drive signal 224, transducer module 206 provides the output force to the skull of the recipient.

For ease of description the electrical signal supplied by transducer drive components 242 to transducer module 206 has been referred to as drive signal 224. However, it should be appreciated that processed signal 224 may comprise an unmodified version of processed signal 226.

As noted above, in one embodiment of the present invention, transducer module 206 generates an output force to the skull that is tangentially directed with respect to the recipient's skull. The generated vibrational force is conducted via anchor system 208 in this embodiment. As shown in FIG. 2B, in one embodiment of the present invention, anchor system 208 comprises a housing coupling 260 and an implanted anchor 262. In this embodiment, housing coupling 260 is used to couple housing 225 to implanted anchor 262. Coupling 260 may be mechanically coupled to transducer 206 or housing 225 such that vibrational forces from transducer 206 or housing 225 will be mechanically transferred to coupling 260. For example, in certain embodiments, coupling 260 is mechanically coupled to transducer 206 and vibration is received directly therefrom. In other embodiments, coupling 260 is mechanically coupled to housing 225 and vibration is applied from transducer 206 through housing 225 to coupling 260. Since, according to this embodiment of the present invention, coupling 260 is mechanically coupled to anchor 262, anchor 262 also vibrates in the tangential direction as described above. The vibration of anchor 262 will then cause the recipient's skull to vibrate, rotating the recipient's skull around the recipient's neck and cause the movement of cochlear fluid to be set in a particular motion, producing sound perceptions as described earlier.

In addition to the mechanical coupling between coupling 260 and anchor 262 described above, certain embodiments of the present invention may also utilize other types of couplings between the recipient's skull and transducer 206. For example, anchor 262 may be magnetically coupled to transducer 206 such that the vibrational forces generated by transducer 206 are transmitted magnetically to anchor 262. Furthermore, although transducer 206 and anchor 262 have been presently described as two separate components, it is to be understood that transducer 206 and anchor 262 as described herein may be manufactured as a single or unitary component or manufactured separately and permanently joined together.

Bone conduction device 200 may further comprise an interface module 212. Interface module 212 includes one or more components that allow the recipient to provide inputs to, or receive information from, elements of bone conduction device 200.

As shown, control electronics 246 may be connected to one or more of interface module 212, sound pickup device 202, sound processor 240 and/or transducer drive components 242. In embodiments of the present invention, based on inputs received at interface module 212, control electronics 246 may provide instructions to, or request information from, other components of bone conduction device 200. In certain embodiments, in the absence of user inputs, control electronics 246 control the operation of bone conduction device 200.

FIG. 3 illustrates the conversion of an input acoustic sound signal into a vibrational force for delivery to the recipient's skull in accordance with embodiments of bone conduction device 200. At block 302, bone conduction device 200 receives an acoustic sound signal. In certain embodiments, the acoustic sound signal is received via microphones 202. In other embodiments, the input sound is received via an electrical input. In still other embodiments, a telecoil integrated in, or connected to, bone conduction device 200 may be used to receive the acoustic sound signal.

At block 304, the acoustic sound signal received by bone conduction device 200 is processed by the speech processor in electronics module 204. As explained above, the speech processor may be similar to speech processors used in acoustic hearing aids. In such embodiments, speech processor may selectively amplify, filter and/or modify acoustic sound signal. For example, speech processor may be used to eliminate background or other unwanted noise signals received by bone conduction device 200.

At block 306, the processed sound signal is provided to transducer module 206 as an electrical signal. At block 308, transducer module 206 converts the electrical signal into a vibrational force configured to be delivered to the recipient's skull via anchor system 208 so as to illicit a hearing perception of the acoustic sound signal.

Figure 4A:
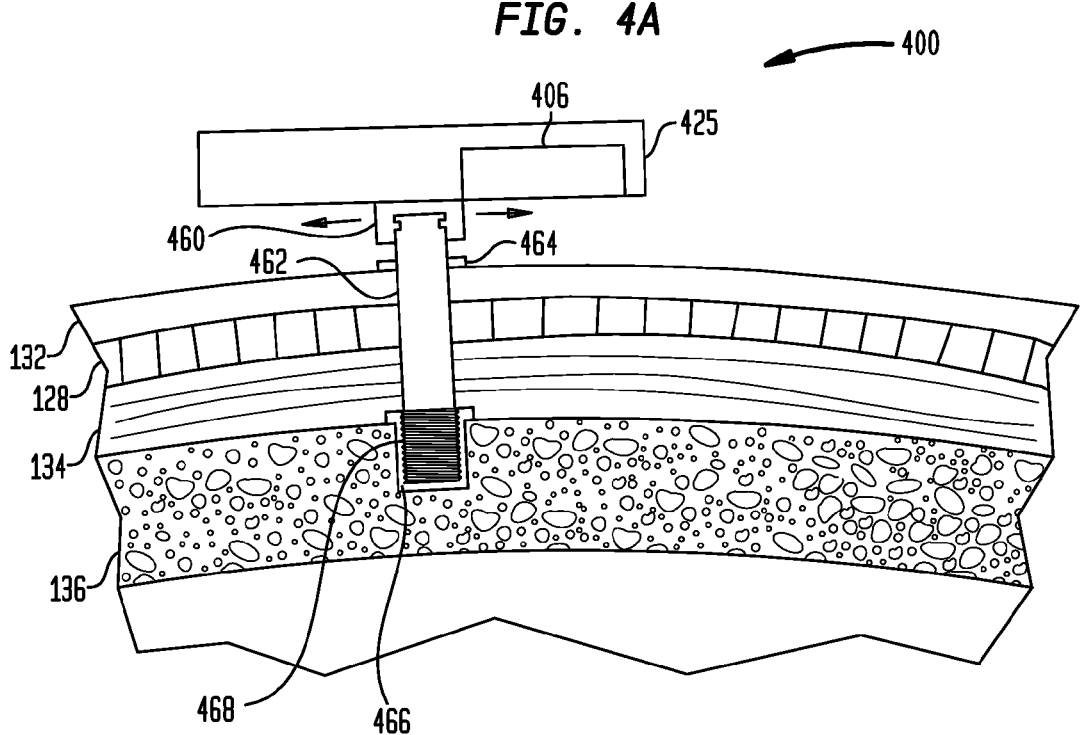
FIG. 4A is a cross-sectional view of a bone-rotating bone conduction device in accordance with embodiments of the present invention.

FIG. 4A illustrates one embodiment of the bone conduction device 400 of the present invention. In the illustrated embodiment, coupling 460 is shown connected to anchor 462. Coupling 460 is configured to deliver the vibrational force, generated tangentially (shown as arrows 401) with respect to the surface of the recipient's skull, from transducer 406 in housing 425 to the recipient's skull 136. The tangentially directed vibrational force acts on the recipient's skull 136 in a way that the recipient's skull is caused to rotate about the recipient's neck. As will be known to persons having skill in the relevant art, the amount of force necessary to cause rotation of the recipient's skull about the recipient's neck will be different and substantially less than the amount of force necessary to cause the recipient's skull to move in a non-rotating side-to-side or up-and-down manner.

Anchor 462 may be attached to recipient's skull 136 in a variety of ways. For example, as illustrated in FIG. 4A, anchor 462 may have a threaded portion 468 at one end which is to be positioned within or adjacent to recipient's skull 136. A corresponding socket 466 may have corresponding threads to receive the threaded portion 468 such that anchor 462 may be screwed into socket 466 to achieve a secure fixation of anchor 462 in recipient's skull 136. Alternatively, in one embodiment, anchor 462 may not have a threaded socket as described above but may instead be screwed directly into correspondingly shaped holes (not shown) formed in recipient's skull 136, wherein the threaded end 468 may have releasable compounds which facilitate in the formation of new bone to surround and securely fix anchor 462 in recipient's skull 136. Other method of securing anchor 462 in recipient's skull 136, now known or later developed, will be obvious to persons having skill in the art and are considered a part of the present invention.

Figure 4B:
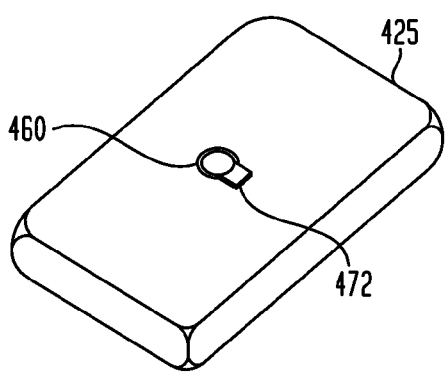
FIG. 4B is a perspective view of components of a bone-rotating bone conduction device in accordance with embodiments of the present invention.
Figure 4C:
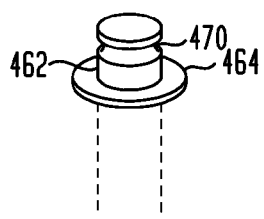
FIG. 4C is a perspective view of other components of a bone-rotating bone conduction device in accordance with embodiments of the present invention.

FIGS. 4B and 4C illustrate in more detail coupling 460 and anchor 462, respectively. As shown, coupling 460 is configured to receive a specifically shaped or configured connection end 470 of anchor 462, shown in FIG. 4C. In the embodiment illustrated in FIG. 4B, latch 472 may be operated to release anchor 462 that has been secured within coupling 460 via connection end 470. In other embodiments of the present invention, other securing and release mechanisms may be used, such as fixation screws which may be screwed in and out to secure and release anchor 462 in coupling 460. Other mechanisms, now known or later developed, will be obvious to person of skill in the art and are considered a part of the present invention.

Also shown in FIGS. 4A and 4C is a ring 464 which is configured to be positioned on the surface of recipient's skin 132 so as to provide a protective shield at the point where anchor 462 emerge through recipient's skin 132. Ring 464 may be made of a flexible material. Ring 464 may also have at least its bottom surface adhered to recipient's skin 132. Furthermore, any gap or space between the hollow center of ring 464 and anchor 462 may be sealed so as to prevent air or moisture from entering or exiting through the opening in recipient's skin 132. By providing ring 464 with a bottom surface adhered to the recipient's skin, and by further sealing any gaps which may otherwise exist between ring 464 and anchor 462, it is possible for the anchor of the present invention to operate over extended periods of time with a greatly reduced risk of liquids and matter entering or leaving the recipient's body, thus reducing various health risks such as infection. Although a relatively simple ring 462 has been described above, it should be understood that more extensive configurations for sealing and securing the recipient's body at the entry point for anchor 462 into the recipient's body may be used in conjunction with embodiments of the present invention.

For the sake of explanation, FIG. 5A illustrates transducer 406, referred to as transducer 506, separately from the various other components of the bone conduction device of the present invention, as described above. In certain embodiments of the present invention, transducer 506 comprises a mass which, when vibrated, moves linearly in a tangential direction with respect to the recipient's skull, thus producing vibrational force that is tangentially directed with respect to the recipient's skull.

In other embodiments of the present invention, the tangentially directed vibrational force is generated by a non-linearly moving mass. FIG. 5B illustrates a first cross-section of the transducer 506 illustrated in FIG. 5A. In the embodiment illustrated, a transducer control circuit 586 and a transducer power module 588 is shown. The embodiment shown in FIGS. 5A-5C may be suitable for implantation in a recipient's skull or embedded under the recipient's skin.

FIG. 5C illustrate a second cross-section of transducer 506, in which a flywheel 592 rotates about a spindle 594 within transducer 506. One or more flywheel magnets and coils 596A-596D (collectively referred to herein as flywheel magnets/coils 596) are disposed around the circumference of flywheel 592. After flywheel 592 has been put in rotational motion, electrical signal 224 energizes flywheel magnets/coils 596, causing flywheel 592 to shift from the original spin-axis extending longitudinally through spindle 594. the magnets/coils 596 are energized according to the electrical signal representing the audio signal received. This shift by flywheel 592 from its original spin-axis will produce a torque vibrational force which is exerted on transducer 506, which then communicates that force to the recipient's skull in the manner described above. The vibrational force will cause the recipient's skull to rotate about the recipient's neck and produce motion in the cochlear fluid, thereby producing sound perception as described above. In one embodiment of the present invention, the vibrational force is generated by the flywheel by rapidly changing or regulating the speed of the flywheel. In other embodiments of the present invention, the vibrational force is generated by the flywheel as its spin-axis is shifted or interrupted as described above. It is to be understood that other techniques for using a flywheel mechanically coupled to the recipient's bone to generate a vibrational force directed tangentially with respect to the recipient's bone are considered a part of the present invention.

Figure 6:
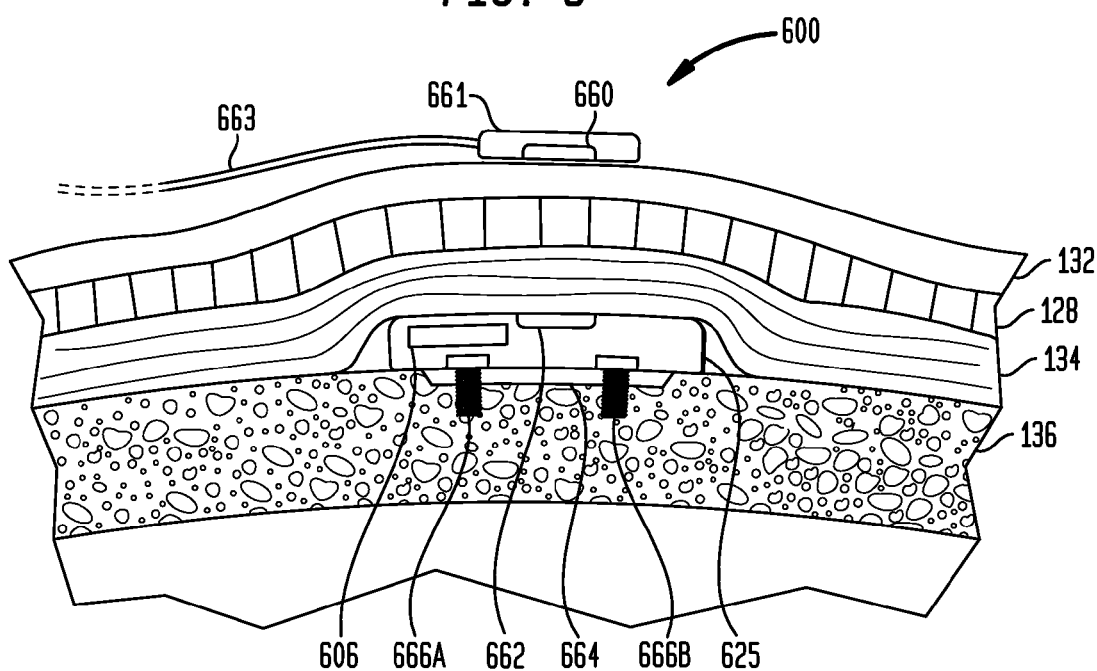
FIG. 6 is a cross-sectional view of a bone-rotating bone conduction device in accordance with other embodiments of the present invention.

FIG. 6 illustrate another embodiment of the present invention in which bone conduction device 100, referred to as bone conduction device 600, comprises an external portion and an implanted portion. In bone conduction device 600, the external portion comprises external housing 661, external communication component 660, and cable 663. Cable 663 may comprise a plurality of leads or cables or optical fibers, and is coupled at one end to housing 661 and external communication component 660 and to, for example, a sound processor (not shown) or a power module (not shown) at the other end. External housing 661 may comprise a securing mechanism (not shown) such as a fixation magnet which magnetically couples to the recipient or to a corresponding fixation magnet (not shown) that is implanted or embedded in the recipient.

External communication component 660 may comprise a communication coil (not shown) which may be configured to at least transmit electrical signal to a receiving component 662 which may comprise an antenna configured to receive the electrical signal transmitted by external communication component 660. Receiving component 662 provides the received electrical signal to various circuits within implanted housing 625, including transducer module 606, for further processing and for use in generating tangentially directed vibrational forces as described in conjunction with other embodiments of the present invention.

In the embodiment illustrated in FIG. 6, the implanted portion also comprises a fixation plate 664 and fixation screws 666A and 666B (collectively referred to as fixation screws 666). As shown, fixation plate 664 is coupled to the recipient's skull by fixation screws 666 which securely retains plate 664 against the recipient's skull. Implanted housing 625 is configured to be coupled to fixation plate 664. Housing 625 and plate 664 may be configured so that housing 625 does not become integrated or otherwise permanently attached the recipient's skull 136 or other tissue. Instead, housing 625 is configured to be coupled to fixation plate 664 in such a manner that it can be removed and replaced with relative ease. For example, clips, screws or compression fit mechanisms may be used to secure housing 625 to fixation plate 664. As described previously in conjunction with other embodiments of the present invention, bone conduction device 600 is used to generate vibrational force in a tangential direction with respect to the recipient's skull such that the recipient's skull is caused to rotate about the recipient's neck and such that the motion causes the recipient's cochlear fluid to be set in a particular motion at audio frequencies, thereby producing sound perception by the recipient. Further features of embodiments of the present invention may be found in U.S. Provisional Patent Application 61/041,185, filed Mar. 31, 2008, which is hereby incorporated by reference herein.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

What is claimed is:

1. A bone conduction device, comprising:
   a sound input element configured to receive an acoustic sound signal;
   an electronics module configured generate an electrical signal representing said acoustic sound signal; and
   a transducer, comprising a mass, configured to generate a rotational vibrational force that is tangential with respect to a surface of a recipient's bone.

2. The device of claim 1, wherein said transducer comprises one or more piezoelectric elements configured to generate said vibrational force.

3. The device of claim 1, further comprising:
   one or more coil and magnet assemblies,
   wherein said mass configured to move in a rotational direction is a flywheel rotating about a spindle,
   and further wherein said one or more coil and magnet assemblies are disposed around the circumference of said flywheel and configured to generate magnet forces on said flywheel when said coil is energized.

4. The device of claim 1, further comprising
   an anchor mechanically coupled to said transducer and configured to receive and transmit said vibrational forces.

5. The device of claim 4, wherein said transducer further comprises a magnet configured to couple said transducer to said anchor.

6. The device of claim 4, wherein said transducer is mechanically coupled to a coupling configured to receive one end of said anchor.

7. The device of claim 4, wherein said one end of said anchor is fixedly attached to the recipient's bone.

8. The device of claim 7, wherein said anchor is configured to be positioned at least partially in the recipient's bone and further configured to osseointegrate with the recipient's bone over a period of time.

9. The device of claim 7, further comprising a fixation plate configured to securely attached to the recipient's bone, wherein said anchor is configured to be coupled to said fixation plate.

10. The device of claim 9, wherein said plate is configured to osseointegrate with the recipient's bone over a period of time.

11. The device of claim 1, wherein the bone conduction device is configured to be attached to a skull of a recipient behind an outer ear of the recipient such that the vibrational force generated by the transducer imparts a rotational force about the recipient's neck.

12. A bone conduction device having an anchor, comprising:
 means for forming a mechanical coupling between the bone conduction device and the recipient's bone;
 means for receiving an electrical signal representative of an acoustic sound signal;
 means for generating a rotational vibrational force representative of the received electrical signal, wherein the vibrational force is directed in a tangential direction with respect to the recipient's bone; and
 means for delivering said vibrational force to the recipient's bone via the formed mechanical coupling.

13. The device of claim 12, wherein the means for generating the vibrational force generates said vibrational force representative of the received electrical signal via a mass configured to move in a rotational path.

14. The device of claim 12, wherein the means for generating the vibrational force includes one or more piezoelectric elements.

15. The device of claim 12, further comprising:
 means for securing an anchor to the bone conduction device.

16. The device of claim 12, further comprising:
 means for attaching the anchor to the recipient's bone.

17. The device of claim 12, wherein:
 the means for generating the vibrational force includes a flywheel.

18. The device of claim 12, wherein:
 the means for generating the vibrational force includes a mass configured to rotate and a means for adjusting a location of a rotational axis of the rotating mass.

19. The device of claim 12, wherein:
 the means for generating the vibrational force includes a mass configured to rotate and a means for adjusting a rotational velocity of the rotating mass.

20. A bone conduction device, comprising:
 a mass configured to rotate about an axis, wherein
 the bone conduction device is configured to adjust at least one of a location, relative to another component of the bone conduction device, of the axis about which the mass rotates, and a rotational velocity of the mass, thereby producing vibrations to evoke a hearing percept in a recipient.

21. The bone conduction device of claim 20, wherein the bone conduction device is configured to exert a torque vibrational force.

22. The bone conduction device of claim 20, wherein the bone conduction device is configured to adjust the location, relative to the another component of the bone conduction device, of the axis about which the mass rotates while the mass is rotating, thereby producing vibrations to evoke the hearing percept in the recipient.

23. The bone conduction device of claim 20, wherein the bone conduction device is configured to adjust the rotational velocity of the mass, thereby producing vibrations to evoke the hearing percept in the recipient.

24. The bone conduction device of claim 20, wherein the bone conduction device is configured to be attached to a skull of a recipient behind an outer ear of the recipient such that the bone conduction device imparts a rotational force about the recipient's neck, thereby evoking the hearing percept.

* * * * *